United States Patent
Cornil

(10) Patent No.: US 9,610,123 B2
(45) Date of Patent: *Apr. 4, 2017

(54) SYSTEM FOR TREATING SKIN WOUNDS, BANDAGING AND BIOCHEMICAL ACTIVATION EQUIPMENT FOR EMPLOYING THIS SYSTEM

(75) Inventor: Alain Cornil, Aix-en-Providence (FR)

(73) Assignee: URGO Recherche Innovation et Developpement, Chenove (FR)

( * ) Notice: Subject to any disclaimer, the term of this patent is extended or adjusted under 35 U.S.C. 154(b) by 845 days.

This patent is subject to a terminal disclaimer.

(21) Appl. No.: 12/227,882

(22) PCT Filed: May 24, 2007

(86) PCT No.: PCT/FR2007/051321
§ 371 (c)(1),
(2), (4) Date: Apr. 29, 2009

(87) PCT Pub. No.: WO2007/138217
PCT Pub. Date: Dec. 6, 2007

(65) Prior Publication Data
US 2010/0004682 A1    Jan. 7, 2010

(30) Foreign Application Priority Data
May 29, 2006    (FR) ..................... 06 51942

(51) Int. Cl.
*A61B 18/20*    (2006.01)
*A61N 5/06*    (2006.01)
(Continued)

(52) U.S. Cl.
CPC ............ *A61B 18/20* (2013.01); *A61B 18/203* (2013.01); *A61N 5/0616* (2013.01);
(Continued)

(58) Field of Classification Search
USPC ..................... 606/14–15, 41, 213–214, 229
See application file for complete search history.

(56) References Cited

U.S. PATENT DOCUMENTS 3,746,814 A * 7/1973 Lackey et al. ............... 200/505
5,156,613 A  10/1992 Sawyer et al.
(Continued)

FOREIGN PATENT DOCUMENTS

| EP | 1 384 446 A | 1/2004 |
| FR | 2 598 088 | 11/1987 |
| WO | WO 97/17025 | 5/1997 |

OTHER PUBLICATIONS

Response to Mar. 15, 2012 Final Office for U.S. Appl. No. 12/087,434 (6 pgs.).
(Continued)

*Primary Examiner* — Lynsey Crandall
*Assistant Examiner* — Manolis Pahakis
(74) *Attorney, Agent, or Firm* — Mintz, Levin, Cohn, Ferris, Glovsky and Popeo, P.C.

(57) ABSTRACT

The present invention concerns a system for dermatologic treatment comprising an energy source for activating a biochemical healing effect and at least one bandage meant to be placed on or near the area being treated before applying the activation step using the said energy source characterized in that the bandage comprises an identification means (4, 5, 10, 11) interacting with a sensor controlling the functioning of the energy source.

7 Claims, 2 Drawing Sheets

Figure 1:
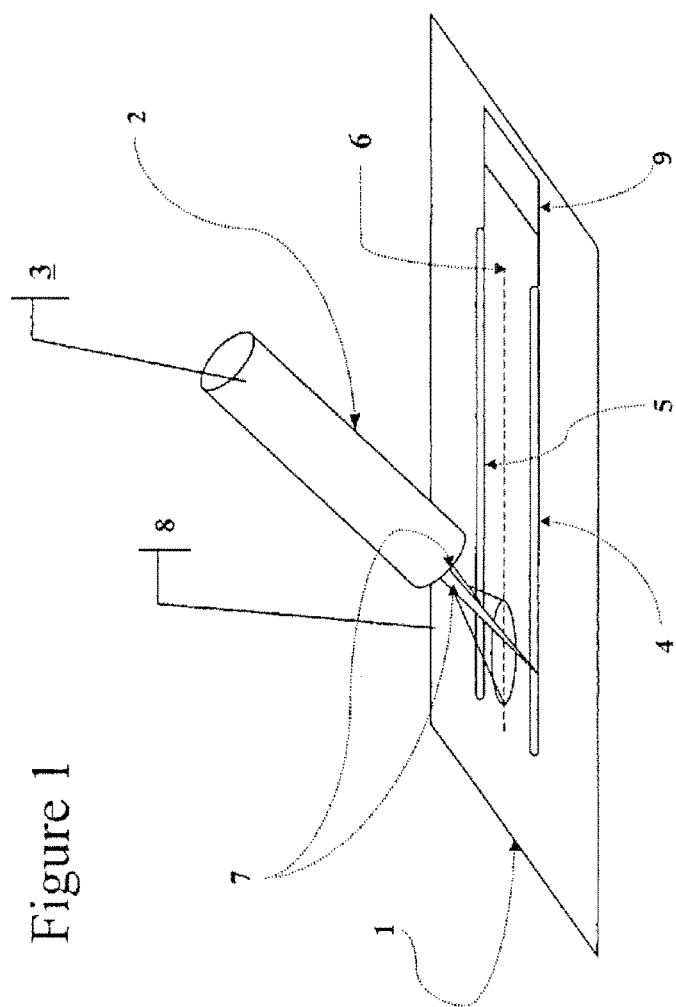

(51) Int. Cl.
*A61B 18/00* (2006.01)
*A61N 5/067* (2006.01)

(52) U.S. Cl.
CPC ..... *A61B 2018/00636* (2013.01); *A61N 5/062* (2013.01); *A61N 2005/067* (2013.01); *A61N 2005/0644* (2013.01)

(56) References Cited

U.S. PATENT DOCUMENTS

| | | | |
|---|---|---|---|
| 5,460,182 A * | 10/1995 | Goodman et al. | 600/342 |
| 5,616,140 A * | 4/1997 | Prescott | 606/10 |
| 6,032,062 A * | 2/2000 | Nisch | 600/372 |
| 6,074,382 A | 6/2000 | Asah et al. | |
| 6,080,160 A * | 6/2000 | Chen et al. | 606/139 |
| 6,312,451 B1 * | 11/2001 | Streeter | 607/89 |
| 6,334,069 B1 * | 12/2001 | George et al. | 607/2 |
| 6,773,699 B1 | 8/2004 | Soltz et al. | |
| 7,100,615 B1 * | 9/2006 | Kert | 128/898 |
| 7,307,530 B2 | 12/2007 | Fabian et al. | |
| 8,944,601 B2 * | 2/2015 | Muehlhoff | A61F 9/00827 351/219 |
| 2002/0111609 A1 | 8/2002 | Mordon et al. | |
| 2003/0018373 A1 * | 1/2003 | Eckhardt | A61L 2/10 607/94 |
| 2004/0133251 A1 * | 7/2004 | Altshuler et al. | 607/88 |
| 2005/0234526 A1 * | 10/2005 | Gilhuly | A61B 1/00142 607/86 |
| 2006/0085049 A1 * | 4/2006 | Cory et al. | 607/48 |
| 2006/0271026 A1 * | 11/2006 | Silvestrini | A61B 3/152 606/4 |
| 2007/0016074 A1 * | 1/2007 | Abreu | A61B 3/1241 600/475 |
| 2007/0179482 A1 * | 8/2007 | Anderson | A61B 18/203 606/9 |
| 2008/0091178 A1 * | 4/2008 | Sunalp | A61B 90/94 606/4 |
| 2008/0138289 A1 * | 6/2008 | Goronkin | A61K 49/0063 424/9.4 |
| 2009/0012515 A1 * | 1/2009 | Hoenig | A61B 18/203 606/33 |
| 2009/0216299 A1 * | 8/2009 | Dantus | 607/89 |
| 2009/0240310 A1 * | 9/2009 | Kennedy | 607/89 |
| 2010/0063489 A1 * | 3/2010 | Cornil | A61B 17/00491 606/8 |
| 2011/0144410 A1 * | 6/2011 | Kennedy | A61K 31/327 600/2 |

OTHER PUBLICATIONS

Final Office Action dated Mar. 15, 2012 for U.S. Appl. No. 12/087,434 (7 pgs.).
Response to Mar. 8, 2011 Final Office Action for U.S. Appl. No. 12/087,434 (9 pgs.).
Final Office Action dated Mar. 8, 2011 for U.S. Appl. No. 12/087,434 (12 pgs.).
Non-Final Office Action dated Oct. 7, 2010 for U.S. Appl. No. 12/087,434 (10 pgs.).
Response to Nov. 12, 2009 Office Action for U.S. Appl. No. 12/087,434 (15 pgs.).
Non-Final Office dated Nov. 12, 2009 for U.S. Appl. No. 12/087,434 (10 pgs.).
International Search Report for International Application No. PCT/FR2006/002462 (2 pgs.).
International Search Report for International Application No. PCT/FR2007/051321 (1 pg), Sep. 18, 2007.
Response to Aug. 1, 2012 Office Action for U.S. Appl. No. 12/087,434 dated Oct. 12, 2012 (5 pgs.).
Non-Final Office Action dated Aug. 1, 2012 for U.S. Appl. No. 12/087,434 (4 pgs.).
Copyright 2007 by Sociedade Brasileira de Angiologia e de Cirurgia Vascular, entitled Effects of low-level laser therapy on the progress of wound healing in humans: the contribution of in vitro and in vivo experimental studies, Adeir Moreira Rocha Junior et al., J Vasc Bras 2007;6(3): 258-266.

* cited by examiner

SYSTEM FOR TREATING SKIN WOUNDS, BANDAGING AND BIOCHEMICAL ACTIVATION EQUIPMENT FOR EMPLOYING THIS SYSTEM

CROSS REFERENCE TO RELATED APPLICATIONS

This application claims benefit to PCT Application No. PCT/FR2007/051321, having an international filing date of May 24, 2007, which claims priority to French patent application no. 0651942, filed May 29, 2006. Each of the foregoing disclosures is expressly incorporated herein by reference in its entirety.

TECHNICAL FIELD

The present invention relates to the repair of skin wounds.

BACKGROUND

Various solutions are known in the prior art, consisting of improving the suture and healing process by using an external energy source. The lips of the wound are brought together and held in place by a dressing, which may include active ingredients that are activatable by the external energy source.

International patent application WO9717025 describes a treatment process consisting of affixing a cross-linked material containing a non-collagenous protein component onto a tissue. This cross-linked material is first placed on a target location on the tissue, and energy is then applied to the cross-linked material. The non-collagenous protein component is such that when energy is applied in an appropriate quantity, the matrix adheres to the tissue.

European patent application EP265470 describes a device for uniting the lips of a wound, comprising a laser whose emission wavelength is chosen such that it can perform tissue bonding and unite the lips of the wound, and a holding piece suitable for being secured to the tissue around the wound so as to hold the lips of said wound in contact, at least while the wound is exposed to said laser radiation. The holding piece includes at least one region suitable for being positioned over the wound and sufficiently transparent at the wavelength of laser radiation for the energy of said radiation to be sufficient, after it has passed through said region, to perform the desired tissue bonding.

The use of activation devices such as a laser source is not without danger and handling such apparatus may cause accidents if the beam is inadvertently directed towards the eye of a person near the operating area.

SUMMARY

The aim of the present invention is to avoid such disadvantages in the prior art.

To this end, in its most general form, the invention relates to a skin wound treatment system comprising an energy source for activating a biochemical effect and at least one dressing designed to be affixed on or close to the wound before the activation stage is performed using said energy source, characterised in that said dressing includes a means of identification that interacts with a sensor that controls the operation of the energy source.

The applications of the invention mainly relate to wound treatment, but also to the field of cosmetic dermatology, with applications such as dermabrasion or laser peeling. The biochemical effect is, in particular, a wound closure effect.

In a preferred variant, the energy source consists of a laser source.

In a first embodiment, the identification means consists of at least one conductive track running the length of said dressing.

In a second embodiment, the dressing is at least partially conductive to form said identification means.

In a preferred embodiment, the identification means consists of two parallel conductive strips running the length of said dressing. In another embodiment, the parallel strips are connected to one another by a conductive track or by means of an electronic memory device containing the identification information. In another embodiment, the two conductive tracks are connected by an electronic memory device in the form of an electronic chip, containing information about the dressing and the firing sequence. This information is read via the two conductive strips.

Advantageously, the identification means consists of a conductive strip running the length of said dressing and a second parallel strip wherein conductive sections are alternated with insulated sections. In another embodiment, the conductive sections may be connected to the conductive strip either directly or via a memory device.

Preferably, the operating settings of the energy source are controlled according to said identifications means.

The invention also provides a dressing for use with such a system, characterised in that it includes a means of identification consisting of at least one conductive strip.

The invention also provides a biochemical activation device for use with such a system, characterised in that it includes an energy source controlled by a calculator that receives a signal from a sensor suitable for interacting with the identification means incorporated in a dressing.

DETAILED DESCRIPTION

The invention will best be understood by reading the following description and referring to the appended illustration, which provides a schematic view of a device as claimed by the invention.

The dressing (1) is formed by a transparent film as described in European patent application EP265470. Dressing (1) presents two conductive strips (4, 5) placed either side of a centre line (6).

It works in cooperation with a laser source (2) controlled by a control unit (3) that supplies power to and controls the laser source. The unit presents extensions (7, 8) whose ends are conductive and which enable the activation system to interact with the conductive tracks (4, 5).

This information can be used to optimise the settings of the associated energy source, in particular the power, duration and frequency of the pulses.

Activation of the laser is dependent on a contact being made between conductive tracks (4, 5) and the ends of extensions (7, 8). If such a signal is not detected, the laser is on standby and thus prevents any risk of accident, even when inadvertently directed towards a person. In some implementations, reference numeral 2 can refer to an active device, reference numeral 4 can refer to a conductive track on the dressing, reference numeral 5 can refer to another conductive track on the dressing, reference numeral 6 can refer to an incision line, reference numeral 7 can refer to a contact connecting the device and the dressing, and reference numeral 9 can refer to a memory device that can contain information for activating the active device 2.

Figure 2:
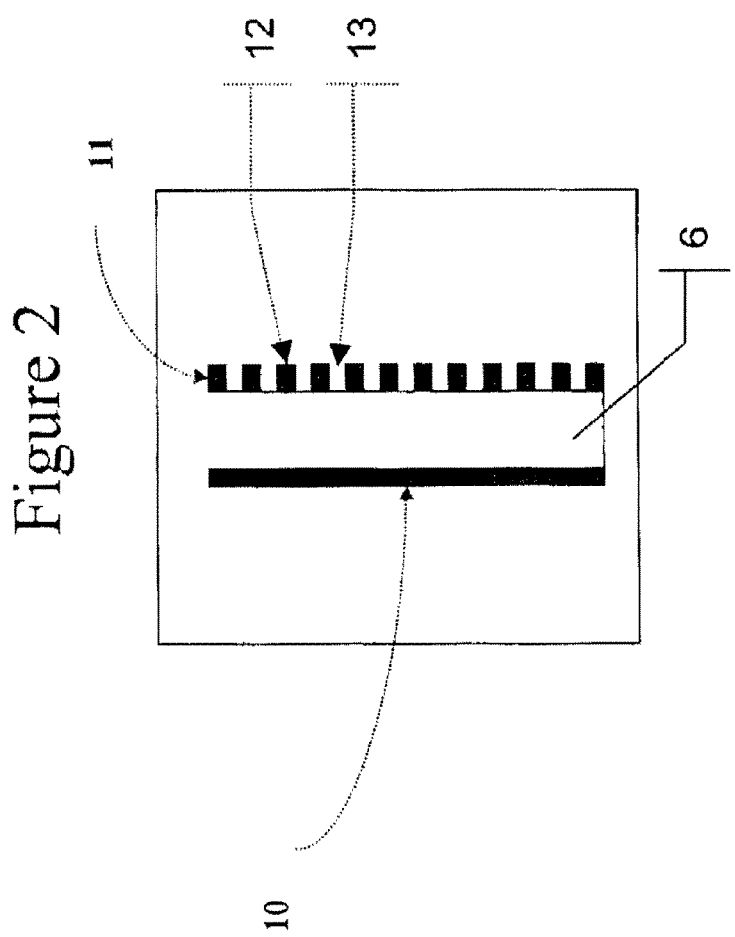

FIG. 2 shows a variant embodiment of the dressing. The dressing presents, on either side of the centre line (6), a first continuous conductive track (10) and a second track (11) with conductive zones (12) alternating with insulated zones (13). In some implementations, each of reference numerals 10 and 11 can refer to a conductive strip.

The alternation between conductive zones (12) and insulated zones (13) is used to control the laser operating settings, for instance periodical activation and deactivation for an operating method involving bursts, or coding for operation according to different dressing types. In the latter case, the alternation between conductive zones (12) and insulated zones (13) constitutes a coding for the dressing type. An initial scan with handpiece (2) is used to identify the dressing and to determine the operating settings accordingly.

Said settings are recorded in the memory of the laser control unit, for instance in the form of a table. These settings may be updated, particularly in the event that a new type of dressing is marketed, via a link with an external computerised device, or by data entry using an input interface incorporated in control unit (3).

In another equivalent variant, the interaction may take place by means of an optical marking, for instance a fluorescent marking, excited by a secondary source fitted in the handpiece. The handpiece in this case includes an optical sensor, for instance a sensor including a CCD (charge-coupled device) associated with a calculator that analyses the image detected in order to calculate the distance and possibly the orientation of the handpiece with respect to the marking on the dressing. This marking may take the form of a matrix code or geometrical figures by which the distance may be deduced on the basis of the size and deformation of the image, as detected by the sensor in the handpiece.

The dressing may consist of a simple transparent film, by which the lips of the wounds are brought together and temporarily held in place and by which the energy provided by the handpiece can be transferred. It may also consist of an opaque film with a transparent window running the length of the centre line (6).

It may also include active coatings involved in the biochemical reactions under the effect of excitation by an energy source.

The energy source described is a laser beam. However, other equivalent energy sources such as ultrasound, radio-frequency electromagnetic waves or a thermal source may be used and would constitute a technical equivalent. Nevertheless, a laser source remains the preferred solution.

The invention claimed is:

1. A dermatological treatment system comprising:
    a handpiece having a proximal end and a distal end;
    a laser source arranged in the handpiece, wherein the laser source is configured to emit laser beam pulses with a wavelength, a power level, a duration, and a frequency;
    a laser control unit arranged in the handpiece, wherein the laser control unit is configured to control the power level, the duration and the frequency of the laser beam pulses;
    an adhesive wound dressing that is transparent in part, wherein the wound dressing is configured to hold lips of a wound together, wherein the laser beam pulses are configured to bond the lips of the wound together or the wound dressing is partially photoactivatable by the laser beam pulses to bond the lips of the wound together;
    a conductive strip along a length of the wound dressing, the conductive strip encoding a wound dressing identification code;
    a conductive extension protruding from the distal end of the handpiece, wherein the conductive extension is configured to contact the conductive strip so as to electrically connect the conductive strip with the laser control unit, and configured to allow the laser beam pulses to reach the wound or the wound dressing from the distal end of the handpiece during said contact;
    wherein the control unit is configured to control the power level, the duration and the frequency of the laser beam pulses based on the wound dressing identification code.

2. The dermatological treatment system of claim 1, wherein the wound dressing includes a second conductive strip running the length of the dressing, said two conductive strips being parallel to one another.

3. The dermatological treatment system of claim 1, wherein the conductive strip comprises alternating conductive sections and insulated sections encoding the identification code.

4. The dermatological treatment system of claim 2, wherein the two conductive strips comprise a memory having stored thereon the identification code.

5. The dermatological treatment system of claim 2, wherein the two conductive strips comprise a memory having stored thereon a firing sequence for the laser source.

6. The dermatological treatment system of claim 1, wherein the laser control unit comprises a memory having stored thereon a table including a correspondence between the identification code and the power level, the duration and the frequency.

7. The dermatological treatment system of claim 1, wherein the conductive extension terminates at a conductive point.

* * * * *